(12) United States Patent
Kruse et al.

(10) Patent No.: US 10,129,944 B2
(45) Date of Patent: Nov. 13, 2018

(54) DAYLIGHT PORTABLE LAMP FOR INSPECTING PAINTED SURFACES, IN PARTICULAR IN THE COURSE OF PAINT REPAIR WORK ON MOTOR VEHICLES

(71) Applicant: SATA GmbH & Co. KG, Kornwestheim (DE)

(72) Inventors: Albrecht Kruse, Stuttgart (DE); Norbert Maier, Allmersbach i.T. (DE); Alexander Tschan, Kornwestheim (DE); Roman Schnabler, Rodenbach (DE)

(73) Assignee: SATA GMBH & CO. KG, Kornwestheim (DE)

( * ) Notice: Subject to any disclaimer, the term of this patent is extended or adjusted under 35 U.S.C. 154(b) by 0 days.

(21) Appl. No.: 15/678,480

(22) Filed: Aug. 16, 2017

(65) Prior Publication Data
US 2018/0054866 A1 Feb. 22, 2018

(30) Foreign Application Priority Data
Aug. 19, 2016 (DE) .................... 20 2016 005 025 U (51) Int. Cl.
*G01N 21/88* (2006.01)
*H05B 33/08* (2006.01)
(Continued)

(52) U.S. Cl.
CPC .......... *H05B 33/0845* (2013.01); *F21L 4/08* (2013.01); *F21V 21/406* (2013.01);
(Continued)

(58) Field of Classification Search
CPC .......... H05B 33/0845; F21V 23/0428; F21V 21/406; F21L 4/08; G01N 21/8806;
(Continued)

(56) References Cited

U.S. PATENT DOCUMENTS

| 4,963,798 A | 10/1990 | McDermott |
| 5,418,419 A | 5/1995 | McGuire |

(Continued)

FOREIGN PATENT DOCUMENTS

| CA | 2299544 A1 | 9/2000 |
| CA | 2527717 A1 | 12/2004 |

(Continued)

OTHER PUBLICATIONS

German Search Report dated May 2, 2017 for Application No. 20 2016 005 026.6.

(Continued)

*Primary Examiner* — Joseph L Williams
*Assistant Examiner* — Jose M Diaz
(74) *Attorney, Agent, or Firm* — Paul D. Bianco; Stephen Bongini; Fleit Gibbons Gutman Bongini & Bianco, PL (57) ABSTRACT

A daylight portable lamp for inspecting painted surfaces, in particular during paint repair work on motor vehicles, has a setting device for setting the light intensity. The setting device has an operating element that can be adjusted between a minimum position and a maximum position, the light intensity being set to a minimum in the minimum position and the light intensity being set to a maximum in the maximum position. When the operating element is arranged in the vicinity of the minimum or maximum position returns automatically to the relevant minimum or maximum position on the basis of a spring restoring force. The operating element can be arranged infinitely variably in at least one transitional adjusting region between the minimum and maximum position without the operating element returning automatically to the minimum or maximum position, so that in the transitional adjusting region the light intensity can be set infinitely variably by the operating element.

28 Claims, 4 Drawing Sheets

(51) Int. Cl.
*G01N 21/25* (2006.01)
*F21L 4/08* (2006.01)
*F21V 21/40* (2006.01)
*F21V 23/04* (2006.01)
*F21Y 115/10* (2016.01)

(52) U.S. Cl.
CPC ....... *F21V 23/0428* (2013.01); *G01N 21/255* (2013.01); *G01N 21/8806* (2013.01); *F21Y 2115/10* (2016.08); *G01N 21/8803* (2013.01); *G01N 2201/0221* (2013.01)

(58) Field of Classification Search
CPC ............. G01N 21/255; G01N 21/8803; G01N 2201/0221; F21Y 2115/10
See application file for complete search history.

(56) References Cited

U.S. PATENT DOCUMENTS

| | | | |
|---|---|---|---|
| 5,746,495 | A | 5/1998 | Klamm |
| 7,679,281 | B2 | 3/2010 | Kim et al. |
| 7,692,136 | B2 | 4/2010 | Blees et al. |
| 8,376,574 | B2 | 2/2013 | Spartano et al. |
| 2007/0247844 | A1 | 10/2007 | Brass et al. |
| 2008/0212319 | A1 | 9/2008 | Klipstein |
| 2010/0090612 | A1* | 4/2010 | Spartano .................. F21L 4/027 315/287 |
| 2011/0204818 | A1* | 8/2011 | Spartano ............ H05B 37/0209 315/294 |
| 2012/0182748 | A1* | 7/2012 | McCaslin .............. A42B 3/044 362/473 |
| 2013/0201671 | A1* | 8/2013 | Marcus .................... F21L 4/00 362/187 |
| 2014/0313706 | A1 | 10/2014 | Itoh et al. |
| 2018/0038577 | A1* | 2/2018 | Jones .................... F21V 14/025 |
| 2018/0050227 | A1 | 2/2018 | Brose |
| 2018/0051860 | A1 | 2/2018 | Maier |

FOREIGN PATENT DOCUMENTS

| | | |
|---|---|---|
| CN | 101080594 A | 11/2007 |
| CN | 201170503 Y | 12/2008 |
| DE | 1034267 B | 7/1958 |
| DE | 1708014 A1 | 4/1971 |
| DE | 2502230 A1 | 10/1975 |
| DE | 10 2004 043 295 A1 | 3/2006 |
| DE | 20 2012 104 684 U1 | 2/2013 |
| DE | 202015005881 U1 | 11/2015 |
| DE | 10 2014 018 940 A1 | 6/2016 |
| DE | 102014018940 A1 | 6/2016 |
| GB | 1427138 A1 | 3/1976 |
| WO | 2006065589 A1 | 6/2006 |
| WO | 2016041994 A1 | 3/2016 |
| WO | 2016096387 A1 | 6/2016 |

OTHER PUBLICATIONS

German Search Report dated May 2, 2017 for Application No. 20 2016 005 025.8.
German Search Report dated May 19, 2017 for Application No. 10 2016 009 956.9.
Office Action dated Jul. 5, 2018 from U.S. Appl. No. 15/678,571.

* cited by examiner

DAYLIGHT PORTABLE LAMP FOR INSPECTING PAINTED SURFACES, IN PARTICULAR IN THE COURSE OF PAINT REPAIR WORK ON MOTOR VEHICLES

FIELD OF THE DISCLOSURE

The disclosure relates to a daylight portable lamp for inspecting painted surfaces, in particular in the course of paint repair work on motor vehicles, the daylight portable lamp having a setting device for setting the light intensity.

BACKGROUND

In various painting work, a visual inspection of painted surfaces is required. This applies in particular to the respraying of motor vehicles. Thus, a visual matching of the color of the newly painted regions with the original surface regions is necessary because, in spite of the paint industry providing detailed mixing specifications for color paints, differences in color can occur in practice. Furthermore, a visual check of already painted surfaces against color charts, color shade panels or comparison panels is often carried out before the painting operation to determine the correct shade of color for the new painting.

Apart from checking shades of color, however, a visual inspection also serves the purpose of ascertaining further properties or defects of a painted surface. By way of example, undesired cloudiness, craters, pinholes, orange peel, fisheyes, sparkling or metallic effects or variations in the coating thickness, etc. may be mentioned.

In the case of paint repair work on motor vehicles, it must also be remembered that the painted vehicle will later be assessed and/or accepted by a customer outside in natural light. It is therefore required that an inspection of painted surfaces on motor vehicles is performed by the painter outside in natural daylight. Since, however, for reasons of environmental protection and for screening off the painting operation, painting work, in particular on motor vehicles, is performed in enclosed areas (painting booths), there is the need for an at least preliminary inspection of the painted surface directly in the working area of the paintshop or workshop. An inspection in enclosed areas under artificial light also has the advantage that it can be performed under constant, reproducible (light) conditions. By contrast, the light conditions outside vary as a result of various influencing factors (weather, daylight, time of year, etc.).

This is the reason for the development of daylight portable lamps, which can produce a light with a relatively high light intensity that is as similar as possible to daylight, so that an authoritative assessment of painted surfaces can be carried out. After completion of the painting operation, the painter can illuminate the painted surface with the portable lamp, inspect the result of his work and, if appropriate, carry out touch-ups or corrections.

DE 10 2014 018 940 A1 discloses such a daylight portable lamp for inspecting painted surfaces in the area of motor vehicle repairs that is distinguished by a light spectrum similar to daylight along with a high light intensity. In the case of the previously known daylight portable lamp, the light intensity that can be produced can be set. The dimmability of the light is of advantage for example in certain applications, such as the visual inspection of highly reflective or very bright surfaces.

SUMMARY

A daylight portable lamp for inspecting painted surfaces that is distinguished by allowing robust handling while having enhanced setting capabilities is disclosed.

The daylight portable lamp according to the disclosure for inspecting painted surfaces, in particular in the area of paint repair work on motor vehicles, has a setting device for setting the light intensity, the setting device comprising an operating element that can be adjusted between a minimum position and a maximum position, the light intensity being set to a minimum in the minimum position of the operating element and the light intensity being set to a maximum in the maximum position.

In many applications of the portable lamp, it is sufficient for the operator to be able to choose between two settings. In many cases, the operator will wish to use the portable lamp with the maximum light intensity. The minimum position also covers many applications in which the maximum light intensity would lead to disturbing effects, such as for example strong reflections.

In order that, when it is in these frequently used "standard positions", the operating element is not inadvertently moved out of position by nothing more than slight contact, it advantageously returns automatically to the respective standard position if it is deflected slightly from these standard positions. Consequently, if the operating element is arranged in the vicinity of the minimum position or maximum position, it returns automatically to the relevant minimum position or maximum position on the basis of a spring restoring force. Moreover, the action of the spring force on the operating element in the standard positions has the effect that it can only be moved from the standard positions by exerting increased force.

However, there are applications in which the operator would like to set the light intensity precisely according to his requirements to values between the minimum light intensity and maximum light intensity. There may also be the need to vary the light intensity slightly when examining one and the same painted location, in order to be able better to detect certain surface effects or defects. For this reason, it is possible in the case of the portable lamp according to the disclosure to arrange the operating element infinitely variably in at least one transitional adjusting region between the minimum position and the maximum position without the operating element returning automatically to the minimum or maximum position, so that in the transitional adjusting region the light intensity can be set infinitely variably by the operating element—at least in a small range of light intensity.

In the case of a preferred exemplary embodiment of the disclosure, the operating element can be arranged in a midway position between the minimum position and the maximum position, the operating element likewise returning automatically to the midway position on the basis of the spring restoring force when it is arranged in the vicinity of the midway position. As a result of the action of the spring force on it, the operating element can also only be moved from the midway position by exerting increased force. The midway position defines a third "standard position", in which the light intensity is set to a midway value.

The at least one transitional adjusting region is preferably formed between the minimum position and the midway position or between the midway position and the maximum position.

In the case of a particularly preferred exemplary embodiment of the disclosure, between the midway position and the maximum position or between the minimum position and the midway position there is formed a further transitional adjusting region, in which the operating element can be arranged infinitely variably without the operating element returning automatically to the minimum, maximum or midway position, so that in the transitional adjusting region the light intensity can be set infinitely variably by the operating element. Consequently, provided altogether are at least three "standard positions" and between them at least two transitional adjusting regions, in which the light intensity can in each case be set infinitely variably in a small range of light intensity.

It is generally conceivable that the light intensity can be set by the setting device from 0% to 100% of the maximum light intensity, i.e. for example, in the minimum position, the portable lamp is off.

In order to be able to provide a compact setting device with relatively small adjustment displacements of the operating element, but at the same time allow a precise variation of the light intensity, in the case of a particularly preferred exemplary embodiment of the disclosure the light intensity can be reduced by means of the setting device only down to a minimum light intensity that is greater than 40%, in particular greater than 50% (specifically even greater than 75%), of the maximum light intensity. By restricting the range in which the light intensity can be dimmed by the setting device, a more accurate setting of the light intensity can be performed in the remaining smaller light intensity range.

The daylight portable lamp preferably comprises at least one head part, which has a light-exit opening, and a handle part, by which an operator can grip the daylight portable lamp for the inspection of painted surfaces.

In the case of an ergonomically preferred exemplary embodiment, the longitudinal axis of the handle part extends substantially perpendicularly to the direction in which the light that can be produced leaves the head part through the light-exit opening. When the operator grasps the handle part, he is holding it approximately perpendicularly to his lower arm (wrist not bent). The direction in which the light leaves the portable lamp is thus directed substantially parallel to the lower arm. This allows the operator to adopt a comfortable position when inspecting surfaces.

The operating element is preferably accommodated in the vicinity of the lighting element. For this reason, it is of advantage if the operating element is arranged in or on the head part. Particularly advantageous handling is obtained by the operating element being adjustable from the rear side of the head part, which is opposite from the light-exit opening.

The operating element may for example be adjusted by a linear movement.

A preferred exemplary embodiment of the disclosure in which, for setting the light intensity, the operating element is mounted rotatably about a rotary setting axis, in particular is rotationally mounted in the head part, is distinguished by a particularly compact and robust type of construction.

A variant in which the rotary setting axis extends substantially parallel to a longitudinal axis of the handle part of the daylight portable lamp should be preferred for reasons of better handling.

In the case of a preferred exemplary embodiment, the daylight portable lamp has in addition to the operating element an on/off switch, by means of which the daylight portable lamp can be switched on and off. Dividing the "switching on/off" and "dimming" functions between two separate assemblies simplifies their structure and also leads to easier handling of the portable lamp. Furthermore, the portable lamp can be switched off without the setting of the light intensity having to be changed.

A variant of the disclosure in which the on/off switch is formed as a toggle switch has proven successful in practice. As a result of the action of the spring force on it, the toggle switch returns preferably automatically from the on position to the off position. It may however also be formed in such a way that it remains in the respective position.

An exemplary embodiment of a daylight portable lamp according to the disclosure in which the operating element and the on/off switch are arranged on the daylight portable lamp in such a way that an operator grasping the daylight portable lamp with one hand by the handle part for inspecting painted surfaces can use the thumb of the same hand to adjust the operating element and can use the index finger of the same hand to actuate the on/off switch is distinguished by a particularly advantageous operating concept. A portable lamp that is suitable for one-handed operation is obtained.

In the case of a particularly preferred exemplary embodiment, the one-handed operation is achieved inter alia by arranging the on/off switch opposite the operating element of the setting device. Furthermore, the on/off switch is preferably arranged at an end region of the handle part on the head side.

In the case of a particularly preferred exemplary embodiment, for producing the spring restoring force on the basis of which the operating element in the vicinity of the minimum, maximum and, if applicable, midway position returns automatically to the related position, the setting device has a slotted link and a spring element acting upon the slotted link. The slotted link and the associated spring element are arranged in such a way that the spring element slides along the slotted link when there is an adjustment of the operating element. The minimum, maximum and, if applicable, midway position are formed by associated recesses in the slotted link. A robust form of construction of the setting device is obtained.

A preferred variant of the disclosure in which the slotted link is arranged on the operating element, preferably on a collar running around a rotary setting axis of the operating element, is distinguished by a compact configuration of the setting device.

A variant in which the collar that forms the slotted link is formed in one piece with the operating element is distinguished by low-cost production.

A preferred exemplary embodiment in which the operating element is formed substantially as a disk and/or the operating element has a protruding actuating lug is distinguished by structural advantages.

For the purpose of a compact form of construction, the operating element is fastened on an adjusting shaft of a potentiometer for rotation therewith, in particular is fastened directly on it, and is rotatable together with the adjusting shaft about the rotary setting axis. In this case, the slotted link is preferably arranged on the side of the operating element that is facing away from the adjusting shaft of the potentiometer. Alternatively or additionally, a rotary mounting for the operating element about the rotary setting axis is provided on that side of the operating element that is facing away from the adjusting shaft.

In the case of a particularly preferred exemplary embodiment that is distinguished by a simple and space-saving form of the spring element, the spring element is formed as a spring arm which is fastened on the inner side of a housing part of the daylight portable lamp. The spring arm is preferably formed in one piece with the housing part.

Increased functional reliability of the setting device is obtained by a second, redundant spring-element/slotted-linked pairing being provided in addition to the first spring-element/slotted-linked pairing. The two spring element/slotted-link pairings are preferably formed structurally identically.

In the case of a preferred exemplary embodiment, the daylight portable lamp has a lighting element for producing the light which comprises one or more light-emitting diodes. Light-emitting diodes are distinguished by low power consumption, short starting times and a long service life.

In particular in the case where light-emitting diodes are used as the lighting means, an exemplary embodiment in which the setting device sets the light intensity in a pulse-controlled manner is distinguished by a longer service life of the lighting means.

It is of advantage for the handling of the daylight portable lamp according to the disclosure if the daylight portable lamp is formed as a cordless lamp operated by a rechargeable battery. A painter can pass the portable lamp along the surface to be investigated unhindered by a connection cable.

Further refinements of the disclosure are the subject of the subclaims and of the exemplary embodiments of the disclosure described below.

BRIEF DESCRIPTION OF THE DRAWINGS

The disclosure is also explained in more detail on the basis of exemplary embodiments with reference to the accompanying figures, in which specifically.

DETAILED DESCRIPTION

Figure 1:
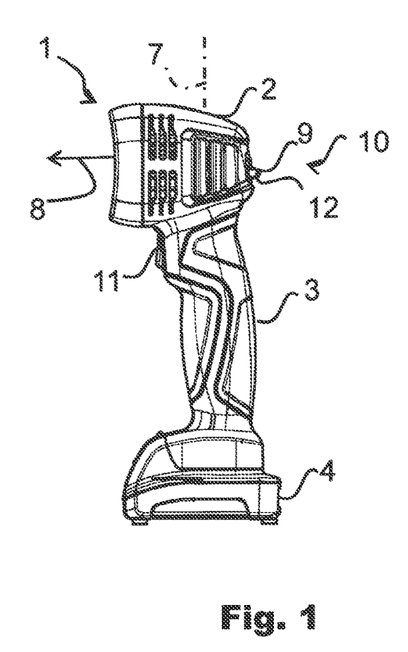
FIGS. 1 to 3 show various perspective views of the daylight portable lamp.
Figure 2:
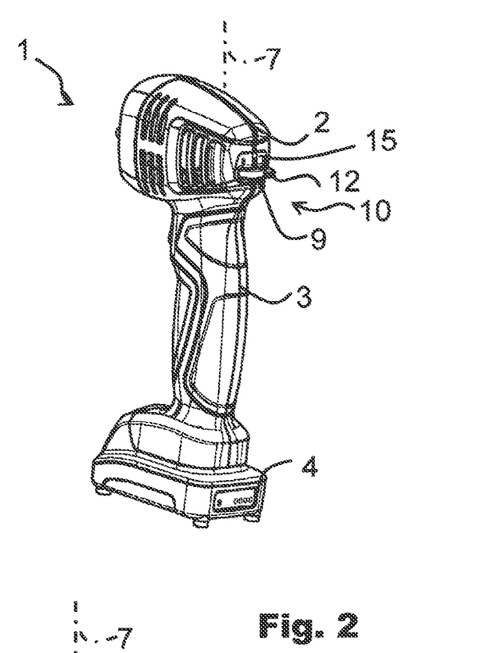
Figure 3:
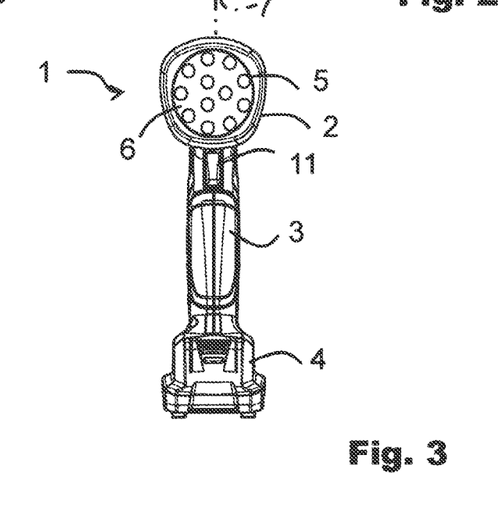

In FIGS. 1 to 3, a daylight portable lamp 1 for inspecting painted surfaces, in particular of paint repair work on motor vehicles, is shown from various viewing directions. The portable lamp 1 has a head part 2, a handle part 3 and, at the lower end of the handle part 3, a detachably fastened Li-ion battery 4. The head part 2 has on its front side a light-exit opening 5, through which the daylight-like light that can be produced can leave. For producing the light, a lighting element 6, which has a number of light-emitting diodes, is arranged in the head part 2.

The longitudinal axis 7 of the handle part 3 extends substantially perpendicularly to the direction 8 in which the light leaves the head part 2 through the light-exit opening 5.

Arranged on the rear side of the head part 2 is an operating element 9 of a setting device 10, by means of which the light intensity of the light produced can be set in a range from 50 to 100% of the maximum light intensity. On the side facing away from the operating element 9, a toggle switch 11 for switching the portable lamp 1 on and off is arranged under the head part 2 on an end region of the handle part 3 on the head part side.

The operating element 9 and the on/off switch 11 are arranged on the daylight portable lamp 1 in such a way that an operator grasping the daylight portable lamp 1 with one hand by the handle part 3 for inspecting painted surfaces can use the thumb of the same hand to adjust the operating element 9 and can use the index finger of the same hand to actuate the on/off switch 11.

The structure and functional principle of the setting device 10 for setting the light intensity are explained in more detail below on the basis of FIGS. 4 to 9.

Figure 4:
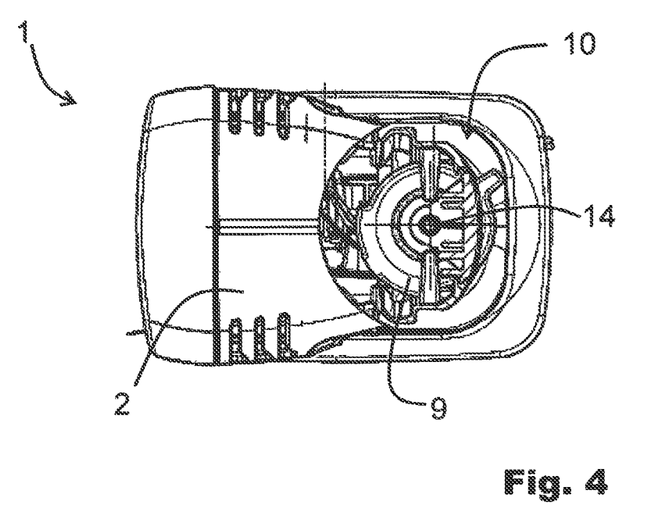
FIG. 4 shows a view from above of the partially sectioned head part of the daylight portable lamp.
Figure 5:
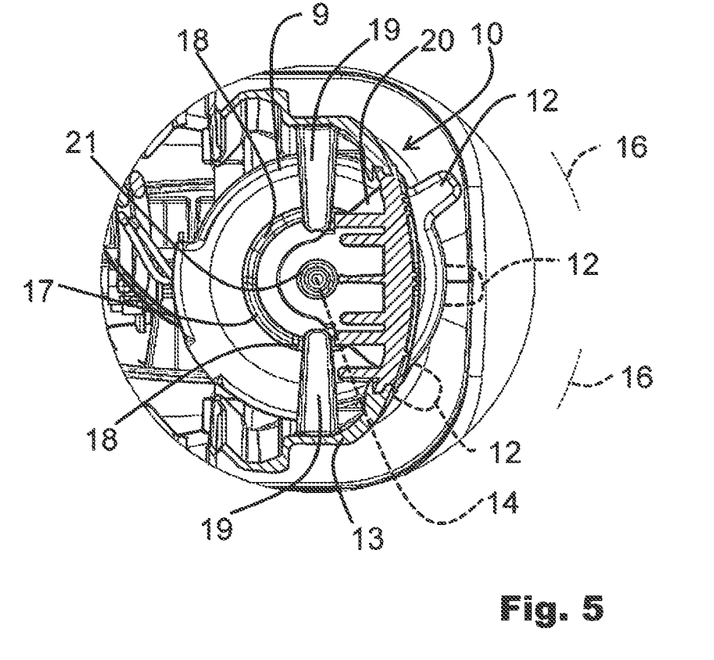
FIG. 5 shows the sectioned partial region of the head part from FIG. 4 in an enlarged representation.

In FIG. 4, a view from above of the partially sectioned head part 2 of the portable lamp 1 is shown. In FIG. 5, the sectioned partial region of the head part 2 from FIG. 4 is shown in an enlarged representation.

The operating element 9, formed substantially as a disk, has a protruding actuating lug 12. The operating element 9 is for the most part arranged and rotatably mounted in the head part 2. The actuating lug 12 protrudes on the rear side of the head part 2 from the housing 13 of the portable lamp 1, so that the operating element 9 can be adjusted by an operator from the rear side of the head part 2. For setting the light intensity, the operating element 9 is mounted rotatably about a rotary setting axis 14, which extends perpendicularly to the plane of the drawing of FIG. 5.

The operating element 9 is shown in FIGS. 4 and 5 in a rotary position that represents the maximum position of the operating element 9. Also indicated in FIG. 5 are further positions of the actuating lug 12, in which the actuating lug 12 is adjusted when the operating element 9 is arranged in rotary positions that correspond to a midway position and a minimum position. In the minimum position of the operating element 9, the light intensity is reduced to the minimum value of about 50% of the maximum light intensity. In the maximum position, the light intensity is set to the maximum. In the midway position, the light intensity is set for example to 75% of the maximum light intensity. When the operating element 9 is arranged in the vicinity of the minimum, maximum or midway position, it returns automatically to the relevant standard position on the basis of a spring restoring force.

On the rear side of the head part 2, identifications 15 for the three standard positions are provided above the protruding actuating lug 12 (FIG. 2). For example, Roman numerals (I, II, III) may be used.

Furthermore, the operating element 9 can be arranged infinitely variably in a transitional adjusting region between the minimum position and the midway position and a transitional adjusting region between the midway position and the maximum position without the operating element 9 returning automatically to one of the standard positions, so that in the transitional adjusting region the light intensity can be set infinitely variably by the operating element 9. In FIG. 5, the transitional adjusting regions are indicated by dashed curved portions 16.

The spring restoring force on the basis of which the operating element 9 in the vicinity of the minimum, maximum and midway position returns automatically to the relevant position is produced as follows.

Two redundant slotted links 18 are formed on a collar 17 that runs around the rotary setting axis 14 and is formed in one piece on the operating element 9. The slotted links 18 are respectively assigned a spring element in the form of a spring arm 19, which acts like a spring on the respective slotted link 18 (directed parallel to the rotary setting axis 14) and, when the operating element 9 turns about the rotary setting axis 14, slides along the assigned slotted link 18. The minimum, maximum and midway positions are formed by associated recesses in the slotted links. The shape of the slotted links can be seen better from FIG. 8, which is explained later.

The spring arms 19 are fastened on the inner side of the housing 13 of the portable lamp 1. Specifically, the spring arms 19 are formed in one piece with a housing part of the portable lamp 1.

By means of a bearing plate 20, which is preferably likewise formed in one piece with a housing part of the portable lamp 1, the operating element 9 is mounted in the head part 2 rotationally about the rotary setting axis 14. For this purpose, a bearing pin 21 formed in one piece with the operating element 9 protrudes through an opening in the bearing plate 20.

Figure 6:
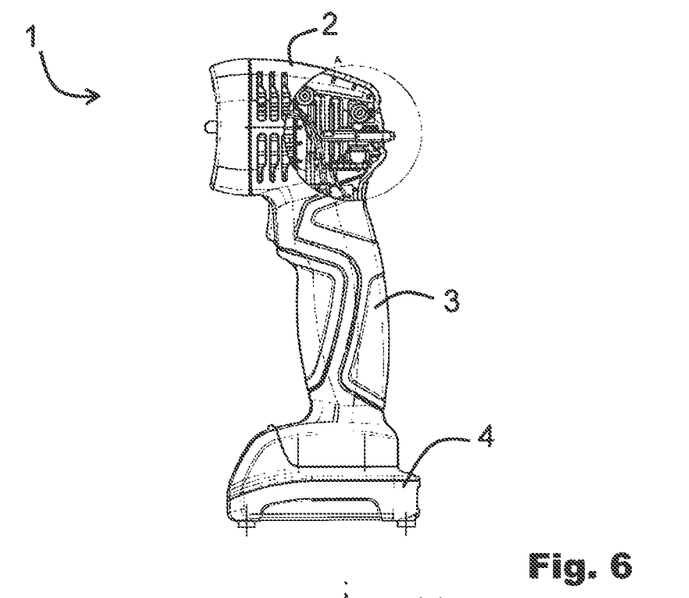
FIG. 6 shows a side view of the daylight portable lamp which is represented partially in section in the region of the head part.
Figure 7:
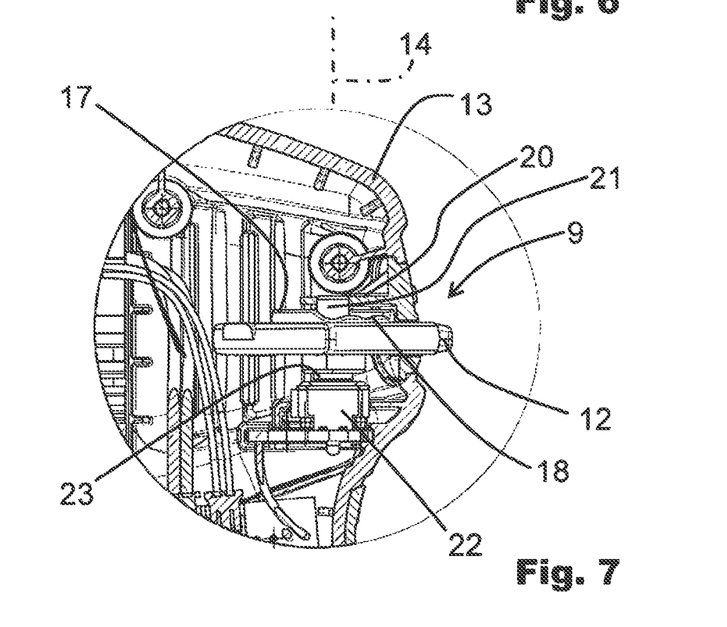
FIG. 7 shows the sectioned partial region of the head part from FIG. 6 in an enlarged representation and FIGS. 8 and 9 show perspective views of an operating element of the setting device of the daylight portable lamp.

It can be seen from FIGS. 6 and 7, which show a partially sectioned side view of the daylight portable lamp 1 and the sectioned partial detail in an enlarged representation, that the rotary setting axis 14 extends substantially parallel to the longitudinal axis 7 of the handle part of the daylight portable lamp 1.

FIG. 7 reveals furthermore that a potentiometer 22, by means of which the voltage applied to the lighting element 6 can be set, whereby in turn the light intensity produced by the lighting element 6 can be set, is arranged under the operating element 9.

The potentiometer 22 is advantageously formed as a rotary potentiometer. On the side that is facing away from the bearing pin 21 and the collar 17, the operating element 9 is fastened on an adjusting shaft 23 of the potentiometer 22 for rotation therewith, in particular is fastened directly on it, and is rotatable together with the adjusting shaft 23 about the rotary setting axis 14. Consequently, the shaft axis coincides with the rotary setting axis 14 for a compact construction. The turning of the adjusting shaft 23 of the potentiometer 22 brings about a pulse-controlled setting of the light intensity produced by the lighting element 6.

Figure 8:
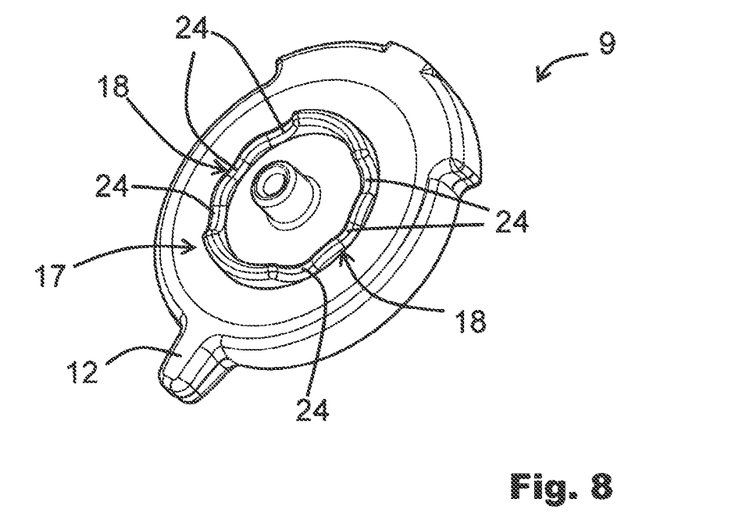
Figure 9:
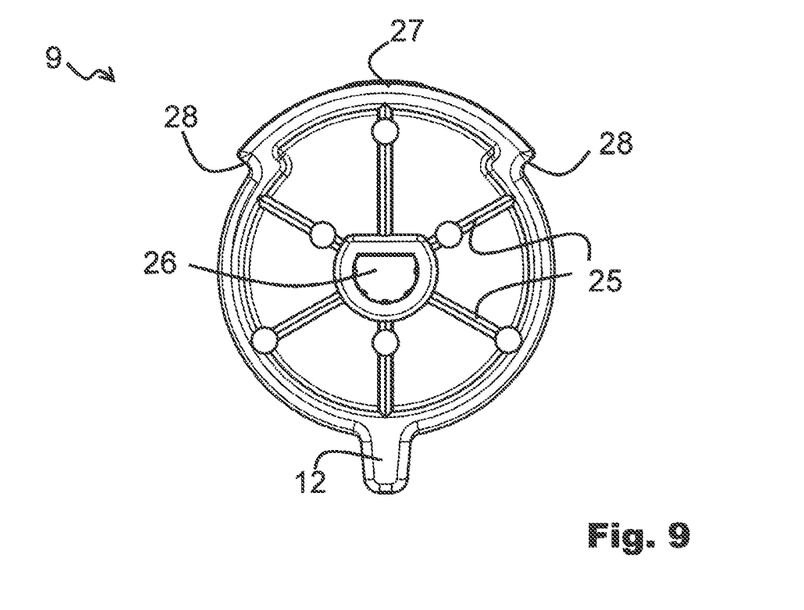

In FIGS. 8 and 9, perspective views of the operating element 9 are shown. In FIG. 8, the side of the operating element 9 on which the running-around collar 17 with the slotted links 18 and the bearing pin 21 are arranged is represented. Each slotted link 18 has three recesses 24, which are respectively assigned to one of the standard positions. In FIG. 9, the opposite side of the operating element 9 is shown. Apart from stiffening struts 25, a clearance 26 is provided in the middle for the rotationally fixed fastening of the adjusting shaft 23.

Furthermore, the operating element 9 has opposite the actuating lug 12 a bulge 27. In the minimum position and maximum position of the operating element 9, the side faces 28 of the bulge 27 come up against stop faces on the housing, and thereby prevent overturning of the operating element 9 beyond the minimum position and the maximum position.

It should be mentioned by way of example that a lighting element may be provided, also having in addition to a cover plate one or more further optical elements (color filters, diaphragms, lenses), which are preferably exchangeable. The optical effects may however also be realized by a cover plate that additionally serves for protecting the internals of the head.

In the case of an application that is not shown, the portable lamp may also be used as a stationary illuminating means. For example, the portable lamp may be attached to a stand, a holder on the ceiling or wall of a painting booth, a tripod, a handling device (robot) or a similar fastening system. Instead of the power being supplied by means of a rechargeable battery, the portable lamp may also be connected by means of an adapter to the power grid, which is for example connected to the portable lamp instead of the battery.

Generally, the portable lamp may also be connected to a control system by a cable or without a cable (for example by Bluetooth). By means of the control system, the portable lamp can for example be switched on and off or the light intensity can be set. In this case, the actuation of the on/off switch and the setting device for the light intensity can be performed under remote control by suitable devices. The on/off switch may also remain in the set position (on or off), it being possible for the light intensity to be remotely controlled or regulated from 0% to 100%.

There may also be sensors (for example color, surface or distance sensors). On the basis of the measurement data of the sensors, the settings of the portable lamp are performed or regulated (for example light intensity distance-dependently).

A separate control system may also provide suggestions, for example for the use of color filters or other optical elements, for the light intensity, etc., with which the portable lamp should be provided or set in order to achieve optimum inspection results. This suggestion may also take place on the basis of sensor data, for example a detection of the color, gloss, distance or surface roughness of the painted surface.

In the case of a further variant that is not shown, a head part of the portable lamp may also be arranged at an angle of 104° with respect to the longitudinal axis of a handle part. This angle has proven to be particularly ergonomic in the case of paint spray guns.

What is claimed is:

1. A daylight portable lamp for inspecting painted surfaces, in particular during paint repair work on motor vehicles, the daylight portable lamp having a setting device for setting the light intensity, the setting device comprising an operating element that can be adjusted between a minimum position and a maximum position, the light intensity being set to a minimum in the minimum position of the operating element and the light intensity being set to a maximum in the maximum position, the operating element when it is arranged in the vicinity of the minimum position or the maximum position returning automatically to the relevant minimum or maximum position on the basis of a spring restoring force, the operating element being able to be arranged infinitely variably in at least one transitional adjusting region between the minimum position and the maximum position without the operating element returning automatically to the minimum or maximum position, so that in the transitional adjusting region the light intensity can be set infinitely variably by the operating element.

2. The daylight portable lamp of claim 1, wherein the operating element can be arranged in a midway position between the minimum position and the maximum position, the operating element likewise returning automatically to the midway position on the basis of the spring restoring force when it is arranged in the vicinity of the midway position.

3. The daylight portable lamp of claim 2, wherein the at least one transitional adjusting region is formed between the minimum position and the midway position or between the midway position and the maximum position.

4. The daylight portable lamp of claim 3, wherein between the midway position and the maximum position or between the minimum position and the midway position there is formed a further transitional adjusting region, in which the operating element can be arranged infinitely variably without the operating element returning automatically to the minimum, maximum or midway position, so that in the transitional adjusting region the light intensity can be set infinitely variably by the operating element.

5. The daylight portable lamp of claim 1, wherein the light intensity can be reduced by the setting device only down to a minimum light intensity that is greater than 40%, in particular greater than 50%, of the maximum light intensity.

6. The daylight portable lamp of claim 1, wherein the daylight portable lamp comprises at least one head part, which has a light-exit opening, and a handle part, by which an operator can grip the daylight portable lamp for the inspection of painted surfaces.

7. The daylight portable lamp of claim 1, wherein the longitudinal axis of the handle part extends substantially perpendicularly to the direction in which the light that can be produced leaves the head part through the light-exit opening.

8. The daylight portable lamp of claim 1, wherein the operating element is arranged in or on the head part, in particular is rotationally mounted in the head part, and the operating element preferably being adjustable from the rear side of the head part, which is opposite from the light-exit opening.

9. The daylight portable lamp of claim 1, wherein for setting the light intensity, the operating element is mounted rotatably about a rotary setting axis.

10. The daylight portable lamp of claim 1, wherein the rotary setting axis extends substantially parallel to a longitudinal axis of the handle part of the daylight portable lamp.

11. The daylight portable lamp of claim 1, wherein the daylight portable lamp has in addition to the operating element an on/off switch, by means of which the daylight portable lamp can be switched on and off.

12. The daylight portable lamp of claim 1, wherein the on/off switch is formed as a toggle switch.

13. The daylight portable lamp of claim 1, wherein the operating element and the on/off switch are arranged on the daylight portable lamp in such a way that an operator grasping the daylight portable lamp with one hand by the handle part for inspecting painted surfaces can use the thumb of the same hand to adjust the operating element and can use the index finger of the same hand to actuate the on/off switch.

14. The daylight portable lamp of claim 1, wherein the on/off switch is arranged opposite the operating element.

15. The daylight portable lamp of claim 1, wherein the on/off switch is arranged at an end region of the handle part on the head side.

16. The daylight portable lamp of claim 1, wherein for producing the spring restoring force on the basis of which the operating element in the vicinity of the minimum, maximum and, if applicable, midway position returns automatically to the related position, the setting device has a slotted link and a spring element acting upon the slotted link, the spring element sliding along the slotted link when there is an adjustment of the operating element, and the minimum, maximum and, if applicable, midway position being formed by associated recesses in the slotted link.

17. The daylight portable lamp of claim 1, wherein the slotted link is arranged on the operating element, preferably on a collar running around a rotary setting axis of the operating element.

18. The daylight portable lamp of claim 1, wherein the collar that forms the slotted link is formed in one piece with the operating element.

19. The daylight portable lamp of claim 1, wherein the operating element is formed substantially as a disk.

20. The daylight portable lamp of claim 1, wherein the operating element has a protruding actuating lug.

21. The daylight portable lamp of claim 1, wherein the operating element is fastened on an adjusting shaft of a potentiometer for rotation therewith, and is rotatable together with the adjusting shaft about the rotary setting axis.

22. The daylight portable lamp of claim 1, wherein the slotted link is arranged on the side of the operating element that is facing away from the adjusting shaft of the potentiometer.

23. The daylight portable lamp of claim 1, wherein a rotary mounting for the operating element about the rotary setting axis is provided on that side of the operating element that is facing away from the adjusting shaft.

24. The daylight portable lamp of claim 1, wherein the spring element is formed as a spring arm which is fastened on the inner side of a housing part of the daylight portable lamp, preferably is formed in one piece with it.

25. The daylight portable lamp of claim 1, wherein a second, redundant spring-element/slotted-linked pairing is provided in addition to the first spring-element/slotted-linked pairing.

26. The daylight portable lamp of claim 1, wherein the daylight portable lamp has a lighting element for producing the light which comprises one or more light-emitting diodes.

27. The daylight portable lamp of claim 1, wherein the setting device sets the light intensity in a pulse-controlled manner.

28. The daylight portable lamp of claim 1, wherein the daylight portable lamp is formed as a cordless portable lamp operated by a rechargeable battery.

\* \* \* \* \*